United States Patent [19]
Kostansek

[11] Patent Number: 6,004,570
[45] Date of Patent: Dec. 21, 1999

[54] DITHIOCARBAMATE FUNGICIDE COMPOSITIONS WITH IMPROVED PROPERTIES

[75] Inventor: Edward Charles Kostansek, Buckingham, Pa.

[73] Assignee: Rohm and Haas Company, Philadelphia, Pa.

[21] Appl. No.: 09/131,943

[22] Filed: Aug. 10, 1998

Related U.S. Application Data

[60] Provisional application No. 60/082,160, Apr. 17, 1998.

[51] Int. Cl.[6] .......................... A01N 25/10; A01N 25/14; A01N 25/24
[52] U.S. Cl. .......................... 424/407; 424/405; 424/409; 424/417; 424/419
[58] Field of Search ...................... 424/405, 407, 424/409, 417, 419; 514/772.2, 950

[56] References Cited

U.S. PATENT DOCUMENTS

| | | | |
|---|---|---|---|
| 3,299,566 | 1/1967 | MacMullen | 47/1.01 R |
| 3,399,991 | 9/1968 | Littler | 504/330 |
| 3,980,463 | 9/1976 | Muramoto et al. | 504/116 |
| 4,110,431 | 8/1978 | Oita . | |
| 4,923,506 | 5/1990 | Huber et al. | 504/116 |
| 5,169,644 | 12/1992 | Molls et al. | 424/497 |
| 5,252,542 | 10/1993 | Allan | 504/323 |
| 5,639,465 | 6/1997 | Huang et al. | 424/409 |
| 5,849,320 | 12/1998 | Turnblad et al. | 424/410 |
| 5,902,589 | 5/1999 | Hall-Hibbitts et al. | 424/400 |

FOREIGN PATENT DOCUMENTS

| | | |
|---|---|---|
| 0245970 A1 | 11/1987 | European Pat. Off. . |
| 245970 A1 | 11/1987 | European Pat. Off. . |
| 1296118 | 5/1962 | France . |
| 1493069 | 7/1967 | France . |
| 1642122 | 7/1970 | Germany . |
| 1056887 | 2/1967 | United Kingdom . |
| 1209996 | 10/1970 | United Kingdom . |

*Primary Examiner*—Robert H. Harrison
*Attorney, Agent, or Firm*—Thomas D. Rogerson

[57] ABSTRACT

This invention is relates to dithiocarbamate fungicide formulations having improved physical properties. The formulations comprise one or more dithiocarbamate fungicides and a water soluble polymer.

8 Claims, No Drawings

DITHIOCARBAMATE FUNGICIDE COMPOSITIONS WITH IMPROVED PROPERTIES

This is a nonprovisional application of prior pending provisional application serial No. 60/082,160 filed Apr. 17, 1998.

This invention is relates to dithiocarbamate fungicide formulations having improved physical properties. Dithiocarbamates and derivatives thereof are a class of fungicides useful in the control of phytopathogenic fungi.

Due, in part, to their physical-chemical properties, dithiocarbamate compositions are often provided in dry form such as, for example, wettable powders, dusts, and granules and as suspension concentrates, such as aqueous flowable formulations. A number of additives have been investigated to improve the efficacy of such formulations through improvements in the composition's physical/chemical properties or to improve the availability of the dithiocarbamate after application. One such additive is polyvinyl alcohol. French Patent 1493069 discloses the use of polyvinyl alcohol ("PVA") with a molecular weight greater than 100,000 daltons and which is greater than 95% hydrolyzed to increase the affinity of a fungicide for foliage. Canadian Patent 1,328,599 discloses the use of PVA with a molecular weight greater than 80,000 to increase the rainfastness of dithiocarbamates.

Unfortunately, medium to high molecular weight PVA causes severe formulation problems with dithiocarbamates which are manifested as low suspensibility and aggregation in dry formulations such as wettable powders and dispersible granules, and gelation in aqueous suspension concentrates. It is generally accepted that medium to high molecular weight is needed for particle adhesion under wet conditions. There is a need, therefore, for dithiocarbamate formulation additives which will provide the advantages of high molecular weight PVA without degrading the physical/chemical properties of the formulation.

I have surprisingly found that even very low molecular weight PVA can impart significant adhesion in dithiocarbamate fungicide formulations while maintaining, or even improving, many physical properties. In addition I have found that low molecular weight PVA disperses dithiocarbamate particles very well on a leaf surface and allows for much better redistribution of these particles under wet conditions than does higher molecular weight PVA. Redistribution is important for the enhanced activity and efficacy of contact fungicides such as the dithiocarbamates.

This invention provides a composition comprising:
  a) one or more dithiocarbamate fungicides; and
  b) polyvinyl alcohol with a molecular weight of from 10,000 to 80,000, a hydrolysis level of 77 percent to 95 percent, and a particle size less than 800 microns.

Preferably, the dithiocarbamate fungicide is selected from mancozeb (a coordination product of zinc ion and manganese ethylene bisdithiocarbamate), maneb (manganese ethylenebisdithiocarbamate), zineb (zinc ethylenebisdithiocarbamate), ziram (zinc dimethyldithiocarbamate), propineb ([[[(1-methyl-1,2-ethanediyl)bis[carbamatothioato]](2-)]zinc homopolymer, metiram (tris[amine-[ethylene bis(dithiocarbamato)]zinc(II)][tetrahydro-1,2,4,7-dithiadiazocine-3,8-dithione] polymer), thiram (bis(dimethylthiocarbamoyl)disulfide), ferbam (ferric dimethyldithiocarbamate), metham (sodium N-methyldithiocarbamate), and dazomet (tetrahydro-3,5-dimethyl-1,3,5-thiadiazine-2-thione). The dithiocarbamate may be in the form of a wettable powder, a dust, a granular, or an aqueous suspension concentrate. Wettable powder or granular formulations are preferred. Furthermore, the composition itself may be in the form of a wettable powder, a dust, a granular, or an aqueous suspension concentrate. The composition may contain from 1% to 95%, by weight, of the dithiocarbamate, preferably 50% to 85%, more preferably 60% to 80%.

PVA polymers useful in this invention have a molecular weight in the 10,000–80,000 Dalton range (i.e., 4% solution viscosity of <20 cp), more preferably in the 10,000–50,000 range, and most preferably in the 15,000–25,000 range. The acceptable PVA hydrolysis level is in the 77–95% range (i.e., saponification index between 150 and 30), more preferably in the 80–90% range, and most preferably in the 86–89% range. The PVA can be added at levels of 0.1–2.0% based on formulation weight. The more preferred range is 0.2–1.0% and the most preferred range is 0.3–0.7% based on formulation weight. For wettable powders, dispersible granules, and other dry formulations, the PVA can be dry blended with the formulation or dissolved in water and blended with an aqueous composition of the dithiocarbamate prior to drying. In the case of aqueous suspension concentrates, the PVA can be dissolved in the aqueous phase at any point in the formulation process. The preferred method is to dissolve the PVA in the aqueous phase in order to ensure uniform distribution of the polymer in the formulation. The average PVA particle size should be less than 800 microns in diameter, more preferably less than 500 microns, and most preferably less than 250 microns in diameter to aid in dissolution.

For some applications, one or more other pesticides may be added to the dithiocarbamates of the present invention, thereby providing additional advantages and effectiveness. When mixtures of pesticides are employed, the relative proportions which are used will depend upon the relative efficacy of each pesticide in the mixture with respect to the fungi, weeds, and insects to be controlled. Examples of other fungicides which can be combined with the dithiocarbamates of the present invention include, for example, (a) nitrophenol derivatives such as dinocap, binapacryl, and 2-sec-butyl-4,6-dinitrophenyl isopropyl carbonate; (b) heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifluzamide, and, quinomethionate; (c) miscellaneous halogenated fungicides such as: chloranil, chlorothalonil, dichlone, chloroneb, dichloran, and polychloronitrobenzenes; (d) fungicidal antibiotics such as: griseofulvin, kasugamycin and streptomycin; (e) miscellaneous fungicides such as: diphenyl sulfone, dodine, methoxyl, 1-thiocyano-2,4-dinitrobenzene, 1-phenylthiosemicarbazide, thiophanate-methyl, and cymoxanil; as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; and pyrimethanil. Examples of insecticides which can be combined with the dithiocarbamates of the present invention include, for example, acephate, aldicarb, alpha-cypermethrin, azinphos-methyl, binapacryl, buprofezin, carbaryl, carbofuran, chlorpyrifos, clofentezine, cyhexatin, cypermethrin, deltamethrin, dicofol, diflubenzuron, dimethoate, dinocap, endosulfan, endothion, esfenvalerate, ethiofencarb, ethion, ethoate-methyl, ethoprop, fenbutatin-oxide, fenoxycarb, fensulfothion, flucycloxuron, flufenoxuron, fosmethilan, hexythiazox, methamidophos, methidathion, methiocarb, methomyl, methyl parathion, mexacarbate, oxamyl, permethrin, phosalone, phosmet, promecarb, pyridaben, resmethrin, rotenone, tebufenozide, thiodicarb, triazamate, and vamidothion. Examples of herbicides which can be combined with the dithiocarbamates of the present invention include, for example; (a) carboxylic acid derivatives, including benzoic acids and their salts; phenoxy and phenyl substituted carboxylic acids and their salts; glyphosate and its salts, and trichloroacetic acid and its salts; (b) carbamic acid derivatives, including ethyl N,N-di (n-propyl)thiolcarbamate and pronamide; (c) substituted ureas, (d) substituted triazines, (e) diphenyl ether derivatives such as oxyfluorfen and fluoroglycofen, (f) anilides such as propanil, (g) oxyphenoxy herbicides, (h) uracils, (i) nitriles, and (j) other organic herbicides such as dithiopyr and, thiazopyr. In the case of herbicides, care must be taken to ensure that the crop to which the composition of the present invention is applied is tolerant of the herbicide.

For agrochemical uses, the compositions of the present invention can be applied as dusts, granulars, wettable powders, or aqueous sprays by methods commonly employed, such as conventional high-volume hydraulic sprays, low-volume sprays, air-blast, and aerial sprays. The dilution and rate of application will depend upon the type of equipment employed, the method and frequency of application desired, the pesticide application rate, and the pests to be controlled. Formulations or diluted formulations of the compositions of this invention may also contain agronomically acceptable adjuvants. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials,* and *McCutcheon's Functional Materials,* all published annually by McCutcheon Division of MC Publishing Company (New Jersey). In addition, the compositions of this invention may include one or more agronomically acceptable carriers. The term "agronomically acceptable carrier" means any substance which can be used to aid the dispersion of the active ingredient of the composition in water, oil, or in a formulation used for controlling pests, such as a dust, without impairing the active ingredient's effectiveness and which by itself has no significant detrimental effect on the soil, equipment, desirable plants, or the agronomic environment.

The compositions of the present invention can also be mixed with fertilizers or fertilizing materials before their application. The compositions and fertilizing material can also be admixed in mixing or blending equipment, or the compositions can be incorporated with fertilizers in granular, wettable powder, dust, or solution concentrate formulations. Any relative proportion of fertilizer can be used which is suitable for the crops to be treated. The compositions of the invention will commonly comprise from 5% to 50% of the fertilizing composition. These compositions provide fertilizing materials which promote the rapid growth of desired plants, and at the same time control pests.

The following examples are illustrative of the invention:

In the following examples, suspensibility, attrition, and efficacy were evaluated using the following general procedures:

Suspensibility Test 2.0 g of the formulation is added to 250 ml water in a 250 ml graduated cylinder (with stopper). The cylinder is inverted 30 times to disperse the particles and then allowed to stand undisturbed for 30 min. The top 225 ml is then siphoned off and the remaining sediment is washed into a drying dish and dried in an oven. % suspensibility is calculated by subtracting the weight of the sediment from 2.0 g, dividing by 2.0 g, then multiplying by 100.

Granule Attrition Test 50 g of dispersible granule formulation is placed in a standard 8 inch sieve pan with 10 steel balls of ⅜ inch diameter. The pan is covered and placed on a Ro-Tap™ shaker for 10 min. of shaking. After removing the steel balls, the resulting powder is poured into the top of a stack of sieves ranging from 250 micron to 45 micron screen size, with a pan at the bottom. The stack is placed on the shaker for 10 min. of shaking. The weight of the powder retained on each sieve is determined and expressed as a percentage of the original 50 g sample.

Tomato Late Blight (TLB, *Phytophthora infestans*) Control Test

Young tomato plants are sprayed with the formulation dispersed in water at the rate of approximately 500 grams active ingredient per hectare. After a drying time of several hours, the plants are submitted to one half or one inch artificial rain. After drying, the plants are inoculated with TLB disease, incubated, and then placed in the greenhouse for 7–10 days. % disease control is assessed visually by estimating the leaf area unaffected by the disease.

EXAMPLE 1

Mancozeb dispersible granules were prepared by spray drying an aqueous slurry of mancozeb (Dithane DF®fungicide, Rohm and Haas Company) containing no PVA (Sample A), 88% hydrolyzed PVA of 18,000 average molecular weight (Sample B) and 88% hydrolyzed PVA of 115,000 average molecular weight (Sample C). PVA levels were 0.5% based on the weight of the final product. Table I shows the physical properties of these samples. Good suspensibility was maintained with the low molecular weight PVA (B), but it was severely degraded with the higher molecular weight PVA (C). Both PVA's improved the wet-out time of the granules. For health and safety reasons, it is desirable to maintain granule integrity under stress and handling in order to minimize dust formation. Therefore, the samples were submitted to 10 min. of agitation with steel balls and they were evaluated for particle attrition using sieve analysis. The ideal granule size for the product is 100–250 microns in diameter. Table I shows that the low molecular weight sample (B) had better granule integrity and formed fewer fines (i.e., granules <100$\mu$ than the standard sample (A). The sample with the higher molecular weight PVA had an unacceptable level of large aggregates which could cause nozzle clogging problems when sprayed.

TABLE I

| Sample | Susp. (%) | Wet-Out Time (sec) | Attrition: Granules >250 μ (%) | Attrition: Granules 100–250 μ (%) | Attrition: Granules 45–100 μ (%) | Attrition: Granules <45 μ (%) |
|---|---|---|---|---|---|---|
| A | 89 | 32 | 2 | 60 | 33 | 4 |
| B | 86 | 8 | 3 | 70 | 24 | 3 |
| C | 33 | 3 | Large Aggregates in sample | | | |

EXAMPLE 2

Two 80% mancozeb wettable powder samples were prepared by dry blending a commercial wettable powder, (Dithane M-45®fungicide) (Sample A) with 0.5% by weight 88% hydrolyzed PVA of 18,000 average molecular weight to form Sample B. These samples were then evaluated for suspensibility, retention on plastic petri dishes after 1 in. rain (visual estimate), and control of tomato late blight (TLB) under wet conditions in the greenhouse. Table II shows the results of the tests. The formulation containing the low molecular weight PVA (B) had both increased rainfastness and disease control compared to the standard formulation while maintaining good suspensibility.

TABLE II

| Sample | Suspensibility (%) | Retention after 1" Rain (%) | TLB Disease Control (%) |
|---|---|---|---|
| A | 78 | 5 | 80 |
| B | 75 | 30 | 95 |

EXAMPLE 3

Three 37% mancozeb suspension concentrates were prepared by mixing a commercial mancozeb suspension concentrate (Dithane F-45®fungicide, Rohm and Haas Company) (Sample A) with 88% hydrolyzed PVA of 18,000 average molecular weight (Sample B), and 88% hydrolyzed PVA of 115,000 average molecular weight (Sample C). PVA levels were 0.15% based on the weight of the final product. Samples were mixed with a standard lab mixer until all of the polymer had dissolved. Table III shows the physical properties of these samples. Even though viscosity decreased with increasing molecular weight of the polymer, gel strength increased to an unacceptable level (i.e., >100 g-cm) with increasing molecular weight. Although rainfastness increased with molecular weight of the PVA (C), disease control of TLB under wet conditions was better for the low molecular weight PVA (B). The better disease control is probably due to the better particle redistribution observed for the low molecular weight PVA (B).

TABLE III

| Sample | Viscosity (cp) | Gel Strength after 2 wks at 40 deg. C. (g-cm) | Retention after 1" Rain (%) | TLB Disease Control (%) |
|---|---|---|---|---|
| A | 540 | 70 | 20 | 72 |
| B | 680 | 90 | 50 | 94 |
| C | 447 | 120 | 75 | 88 |

EXAMPLE 4

Three 80% maneb wettable powder samples were prepared by dry blending a commercial wettable powder (Dithane M-22®fungicide, Rohm and Haas Company) (Sample A) with 0.5% by weight 88% hydrolyzed PVA of 18,000 average molecular weight to form Sample B and 0.5% by weight 88% hydrolyzed PVA of 155,00 average molecular weight to form Sample C. These samples were then evaluated for suspensibility and retention on plastic petri dishes after 0.5 in. rain (visual estimate). Table IV shows the results of the tests. The formulation containing the low molecular weight PVA (B) had both increased suspensibility and rainfastness compared to the sample with high molecular weight PVA (C). The PVA (B) formulation also had significantly increased rainfastness compared to the standard formulation (A) while maintaining good suspensibility.

TABLE IV

| Sample | Suspensibility (%) | Retention after 0.5" Rain (%) |
|---|---|---|
| A | 86 | 5 |
| B | 78 | 50 |
| C | 51 | 40 |

I claim:

1. A dithiocarbamate fungicide composition comprising:

a) from 1 to 95%, by weight, of one or more dithiocarbamate fungicides; and b) polyvinyl alcohol with a molecular weight of from 10,000 to less than 80,000 Daltons, a hydrolysis level of 77 percent to 95 percent, and a particle size less than 800 microns;

wherein the amount of polyvinyl alcohol is sufficient to provide:

i) increased rainfastness or redistribution of particles on a leaf surface, or ii) improved suspensibility or resistance to granule attrition; when compared with a similar composition without polyvinyl alcohol.

2. The composition of claim 1 wherein the composition is in the form of a wettable powder, a dust, a granular, or a suspension concentrate formulation.

3. The composition of claim 1 wherein the dithiocarbamate is in the form of a wettable powder, a dust, a granular, or a suspension concentrate formulation.

4. The composition of claim 1 wherein the dithiocarbamate is mancozeb, maneb, zineb, ziram, propineb, metiram, thiram, ferbam, metham, or dazomet.

5. The composition of claim 1 further comprising an agronomically acceptable carrier.

6. The composition of claim 1 wherein the polyvinyl alcohol has a molecular weight of from 10,000 to 50,000.

7. The composition of claim 1 wherein the polyvinyl alcohol has a hydrolysis level of from 80 to 90 percent.

8. The composition of claim 1 wherein the polyvinyl alcohol comprises from 0.1 to 2 percent of the total weight of the composition.

* * * * *